(12) United States Patent
O'Neil et al.

(10) Patent No.: US 6,306,172 B1
(45) Date of Patent: Oct. 23, 2001

(54) MODULAR TIBIAL INSERT FOR PROSTHESIS SYSTEM

(75) Inventors: Michael J. O'Neil, West Barnstable; Joseph Kennedy, Lakeville; James Boyko, Attleboro; George Cipolletti, Duxbury, all of MA (US)

(73) Assignee: Johnson & Johnson Professional, Inc., Raynham, MA (US)

( * ) Notice: Subject to any disclaimer, the term of this patent is extended or adjusted under 35 U.S.C. 154(b) by 0 days.

(21) Appl. No.: 09/239,496

(22) Filed: Jan. 28, 1999

(51) Int. Cl.[7] ........................................ A61F 2/38
(52) U.S. Cl. ................................. 623/20.15; 623/20.33
(58) Field of Search ................................ 623/20.15, 20.33, 623/20.25, 20.29, 20.28

(56) References Cited

U.S. PATENT DOCUMENTS

| | | | |
|---|---|---|---|
| 4,219,893 | 9/1980 | Noiles | 3/1.911 |
| 4,257,129 | 3/1981 | Volz | 3/1.911 |
| 4,301,553 | 11/1981 | Noiles | 3/1.911 |
| 4,769,039 | 9/1988 | Horber | 623/20 |
| 5,019,103 | 5/1991 | Van Zile et al. | 623/20 |
| 5,059,216 | 10/1991 | Winters | 623/20 |
| 5,062,852 | 11/1991 | Dorr et al. | 623/20 |
| 5,071,438 | 12/1991 | Jones et al. | 623/20 |
| 5,171,283 | 12/1992 | Pappas et al. | 623/20 |
| 5,395,401 | 3/1995 | Bahler | 623/20 |
| 5,413,605 | 5/1995 | Ashby et al. | 623/20 |
| 5,489,311 | 2/1996 | Cipolletti | 623/20 |
| 5,609,641 | 3/1997 | Johnson et al. | 623/20 |
| 5,658,342 | * 8/1997 | Draganich et al. | 623/20.33 |
| 5,683,469 | 11/1997 | Johnson et al. | 623/20 |
| 5,702,466 | * 12/1997 | Pappas et al. | 623/20.33 |
| 5,776,200 | 7/1998 | Johnson et al. | 623/20 |
| 5,957,979 | * 9/1999 | Beckman et al. | 623/20.33 |

FOREIGN PATENT DOCUMENTS

| | | | |
|---|---|---|---|
| 0495340 | 7/1992 | (EP) | A61F/2/38 |
| 0529408 | 3/1993 | (EP) | A61F/2/38 |
| 0531263 | 3/1993 | (EP) | A61F/2/38 |
| 0627202 | 12/1994 | (EP) | A61F/2/38 |
| 0631764 | 1/1995 | (EP) | A61F/2/30 |
| 0781534 | 7/1997 | (EP) | A61F/2/38 |
| 2716619 | 9/1995 | (FR) | A61F/2/38 |
| 9420047 | 9/1994 | (WO) | A61F/2/38 |
| 9709939 | 3/1997 | (WO) | A61B/17/58 |

* cited by examiner

*Primary Examiner*—Bruce Snow
(74) *Attorney, Agent, or Firm*—Nutter, McClennen & Fish, LLP

(57) ABSTRACT

A modular joint prosthesis includes a tibial component formed of a tibial bearing insert and a tibial plateau. The tibial bearing insert is a modular component formed of a tibial insert body and a modular element. The tibial insert body and the modular elements are provided in a variety of geometries and sizes to yield various types of tibial insert bodies. The same tibial insert body may be used, for example, to form both rotatable and non-rotatable tibial bearing inserts.

23 Claims, 4 Drawing Sheets

MODULAR TIBIAL INSERT FOR PROSTHESIS SYSTEM

CROSS-REFERENCE TO RELATED APPLICATIONS

Not Applicable.

STATEMENT REGARDING FEDERALLY SPONSORED RESEARCH

Not Applicable.

BACKGROUND OF THE INVENTION

The invention relates to joint knee prostheses. More particularly, the invention is directed to tibial components of rotatable and non-rotatable knee joint prostheses that have a modular tibial bearing insert.

Joint replacement surgery is quite common and enables many individuals to function normally when otherwise it would not be possible to do so. Artificial joints usually comprise metallic, ceramic and/or plastic components that are fixed to existing bone.

Knee arthroplasty is a well known surgical procedure by which a diseased and/or damaged natural knee joint is replaced with a prosthetic knee joint. Typical knee prostheses include a femoral component, a patella component, a tibial tray or plateau, and a tibial bearing insert. The femoral component generally includes a pair of laterally spaced apart condylar portions, the distal surfaces of which articulate with complementary condylar elements formed in a tibial bearing insert.

The tibial tray is mounted within the tibia of a patient. Typically, the tibial bearing insert, which is usually made of ultra high molecular weight polyethylene (UHMWPE), is mounted upon the superior surface of the tibial plateau. The geometry of the tibial bearing insert varies depending upon the needs and joint condition of a patient. Some other tibial bearing inserts are designed to be used with joint prostheses that are implanted during procedures that retain the cruciate ligaments. Others are implanted after removal of the cruciate ligaments, and are thus structured to compensate for the loss of these ligaments. Yet other tibial bearing inserts are used with prostheses that provide enhanced stabilization to the knee joint. In addition to the geometry that may be assumed by a tibial bearing insert of a joint prosthesis, the tibial bearing insert may be designed so as to be fixed or rotatable with respect to the tibial plateau upon which it is mounted.

It is not normally possible for a surgeon to make a final determination in advance of surgery the type of knee prosthesis system that will best suit a patient. This decision is not made until the condition of the knee is assessed in the course of surgery.

As a result of the numerous candidate designs for knee joint prostheses, each of which may have a different geometry and varying degrees of constraint and thickness, numerous prosthesis components of differing designs may be used or trialed during a surgical procedure before the appropriate components are selected. Accordingly, a large inventory of parts is required during a joint replacement surgical procedure, thus adding to the cost of surgery. It would thus be advantageous to provide a joint prosthesis system that utilizes modular components to reduce the overall inventory count and to reduce the inventory carrying costs associated with joint replacement surgery.

SUMMARY OF THE INVENTION

The present invention provides a knee joint prosthesis system which utilizes modular tibial bearing insert components. The system includes various components that may be combined to change the structure and functionality of the joint prosthesis.

The prosthesis system of the invention comprises one or more tibial plateaus, one or more tibial insert bodies, and a variety of modular elements that may be combined with one of the tibial insert bodies to yield a suitable tibial bearing insert.

Each tibial plateau has a bottom, bone-engaging surface and a top surface that is matable with a tibial bearing insert. Depending upon the type of tibial bearing insert with which it is to be used, the tibial plateau may or may not include a cavity formed in its top surface.

As noted above, a selection of tibial insert bodies may be provided, each with a different structure and functionality. For example, tibial insert bodies that are suitable for use as rotatable and non-rotatable cruciate retaining tibial inserts may be provided. Other tibial insert bodies include those suitable for use as cruciate retaining tibial bearing inserts, cruciate substituting tibial bearing inserts, and stabilized tibial bearing inserts. The tibial insert bodies may be provided in different sizes as well.

Each tibial insert body has a top articulation surface and a bottom, mating surface that has a cavity formed therein. Various types and sizes of tibial insert bodies may be provided to enable the formation of a variety of tibial bearing inserts.

The modular elements, each of which has a different shape, size and function, are adapted to be inserted within the cavity of the tibial insert body to form a tibial bearing insert of a desired structure and functionality.

One example of a suitable modular element is a plug member that is useful with a non-rotatable cruciate retaining tibial insert body to provide a non-rotatable cruciate retaining tibial insert by simply filling the cavity in the insert body. The modular element may also be in the form of a modular rotating platform post having a plug portion matable with the cavity of the tibial insert and a second portion that extends distally from the plug portion and which is matable within a cavity formed in the top surface of a tibial plateau. Additional modular elements include modular pin elements for forming non-rotatable cruciate substituting tibial inserts and modular rotatable platform posts for cruciate substituting tibial inserts. The modular element may also be in the form of elongate stabilizing pins for use with rotatable and non-rotatable stabilizing tibial inserts.

BRIEF DESCRIPTION OF THE DRAWINGS

The invention will be more fully understood from the following detailed description taken in conjunction with the accompanying drawings, in which.

DETAILED DESCRIPTION OF THE INVENTION

The invention provides a modular tibial component 10 of a joint prosthesis system. The modularity of the system allows basic components to be combined with one or more modular elements to provide increased versatility for the system and to decrease the overall part inventory. Various types of tibial bearing inserts, both rotatable and non-rotatable, can be formed by combining a tibial insert body with an appropriate modular element.

Figure 1:
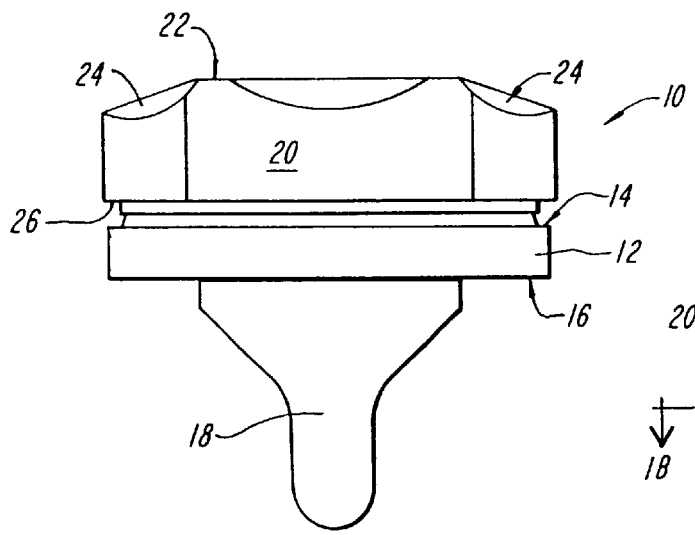
FIG. 1 is an anterior view of a representative modular tibial component modular tibial bearing insert according to the present invention.
Figure 1A:
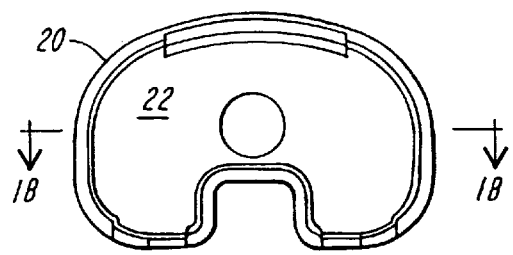
FIG. 1A is a bottom (distal) view of a modular tibial bearing insert used with the tibial component of FIG. 1.
Figure 1B:
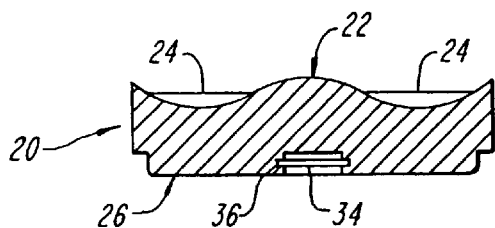
FIG. 1B is sectional view of the modular tibial bearing insert of FIG. 1A at line 1B—1B.
Figure 2A:
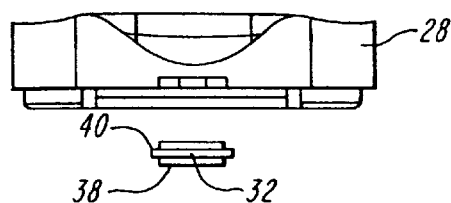
FIG. 2A is an exploded view of the modular tibial bearing insert of FIG. 2 showing a tibial insert body and a spacer plug.
Figure 2:
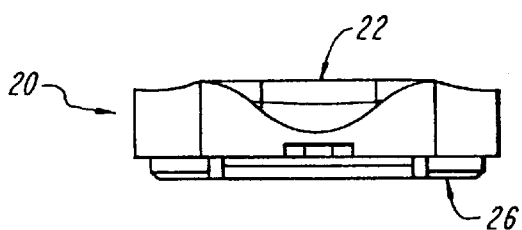
FIG. 2 is an anterior view of the modular tibial bearing insert of FIG. 1B.

FIG. 1 illustrates a tibial component of a representative joint prosthesis system according to the present invention. The tibial component 10 includes a tibial plateau 12 having a top, mating surface 14 and a bottom, bone engaging surface 16 which includes a distally protruding mounting stem 18. A tibial bearing insert 20 is mounted upon the top surface 14 of the tibial plateau. The tibial bearing insert 20 includes a top, articulation surface 22 having at least one concavity 24 adapted to articulate with a condylar element of a femoral component (not shown). The tibial bearing insert 20 also includes a bottom surface 26 which mates upon the top surface 14 of the tibial plateau.

FIGS. 1A through 2A illustrate one type of tibial bearing insert 20 useful with the system of the invention. The tibial bearing insert 20 is formed from a tibial insert body 28 and modular element in the form of a spacer plug 32. The tibial insert body 28 is essentially a precursor to the tibial bearing insert 20. The tibial insert body 28 includes in its bottom surface 26 a cavity 34. The cavity 34 may include surface features 36, or other structures (not shown), suitable to engage the spacer plug 32 to be secured therein. A tibial bearing insert 20 is formed upon securing the spacer plug 32 within the cavity 34 of the tibial insert body 28.

As noted above, a feature of the invention is the modular nature of the prosthesis system, enabling a reduced inventory count as tibial components having different structures and functions are able to be formed from modular components. The system may include tibial insert bodies and modular elements of various styles and sizes. The tibial bearing insert 20 and tibial insert body 28 illustrated in FIGS. 1A through 2A are suitable for use as non-rotatable cruciate-retaining tibial components of a knee joint prosthesis. The spacer plug 32 used to form the non-rotatable cruciate-retaining tibial component is merely a filler for the cavity 34. Once the spacer plug 32 is installed within the cavity 34, the bottom surface 38 of spacer plug 32 is substantially flush with the bottom surface 26 of the tibial bearing insert 20. In the illustrated embodiment, the spacer plug 32 has surface features 40 that cooperate with complementary surface features 36 within cavity 34 to retain the plug within the bore. One of ordinary skill in the art will appreciate that various other structures and/or surface features may be used to retain the plug securely within the bore.

Once the spacer plug 32 and the tibial insert body 28 are assembled to form the cruciate-retaining tibial bearing insert, the tibial bearing insert can be installed upon a tibial plateau in a known manner, e.g., by snap fitting the tibial bearing insert upon the tibial plateau. FIG. 1 illustrates a representative tibial component in which a cruciate retaining tibial bearing insert is mounted upon a tibial plateau.

Figure 3:
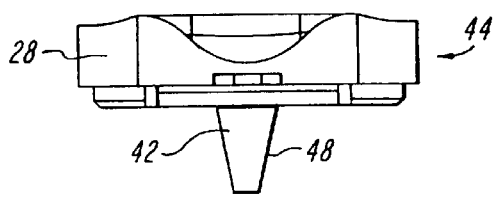
FIG. 3 is an anterior view of another embodiment of a modular tibial bearing insert according to the present invention.
Figure 3A:
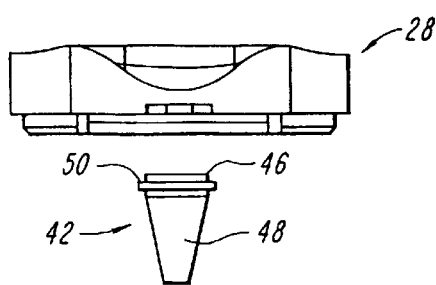
FIG. 3A is an exploded view of the modular tibial bearing insert of FIG. 5 showing a tibial insert body and a rotatable platform post insert element.

FIGS. 3 and 3A illustrate the versatility achieved by the system of the present invention when utilizing a modular rotatable platform post 42 as a modular element in place of spacer plug 32. The tibial insert body 28 shown in FIG. 3A is identical to that shown in FIG. 2A and both will yield cruciate-retaining tibial bearing inserts.

The modular rotatable platform post 42 shown in FIGS. 3 and 3A is useful to form a rotatable cruciate-retaining tibial bearing insert 44. The modular rotatable platform post 42 includes a first, plug portion 46, at a proximal end thereof, and a second, frustoconical portion 48 extending distally from the plug portion. The plug portion 46 should be of a shape and of dimensions so as to enable it to fit securely within cavity 34 of the tibial insert body 28. In the illustrated embodiment, the plug portion 46 is similar in size and shape to the spacer plug 32 described above. That is, the plug portion 46 may include surface features 50 that enable a secured fit within cavity 34.

The frustoconical portion 48 extends distally from the plug portion 46 over a distance of about 10 to 50 mm. The diameter of the frustoconical portion preferably tappers distally from the largest diameter in the range of about 10 to 25 mm to a smallest diameter in the range of about 5 to 20 mm.

The use of modular rotatable platform post 42 enables the tibial insert body 28 to be used as a rotatable cruciate retaining tibial bearing insert. Following assembly of the modular rotatable platform post 42 and the tibial insert body 28 to yield a rotatable cruciate retaining tibial bearing insert, the tibial bearing insert can be mated to a suitable tibial plateau in a manner well known to those having ordinary skill in the art.

Figure 4:
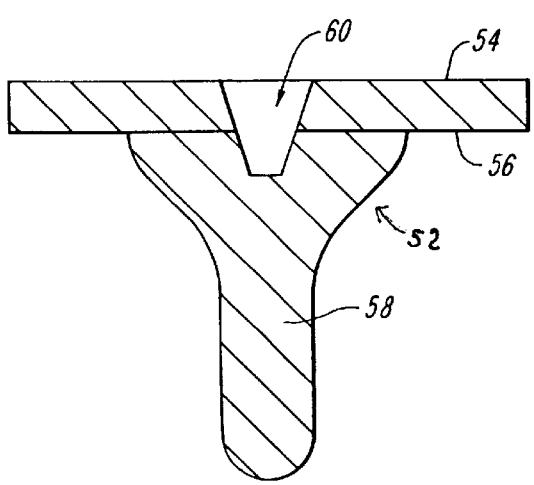
FIG. 4 is a sectional view of a tibial plateau component useful with a rotatable modular tibial bearing insert.

FIG. 4 illustrates a representative tibial plateau 52 that is suitable for use with a rotating tibial bearing insert such as that shown in FIG. 3. Tibial plateau 52 includes a top surface 54 and bottom surface 56 with a mounting stem 58 extending distally therefrom. The top surface 54 of the tibial plateau includes a cavity 60 that extends distally into the tibial plateau. In one embodiment, illustrated in FIG. 4, the cavity 60 is distally tapered with dimensions sufficient to seat the frustoconical portion 48 of the modular rotatable platform post. The tibial bearing insert mounts upon the tibial plateau by seating the frustoconical portion 48 within cavity 60. The relative dimensions of the frustoconical portion 48 and cavity 60 can be readily determined by one having ordinary skill in the art, and they should be such that the tibial bearing insert is able to rotate with respect to the tibial plateau.

Figure 5:
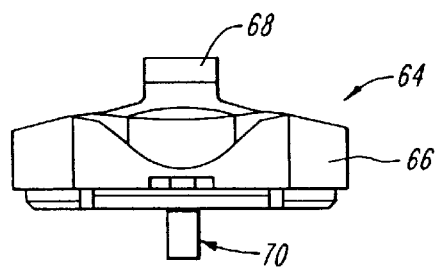
FIG. 5 is an anterior view of another modular tibial bearing insert according to the present invention.
Figure 6:
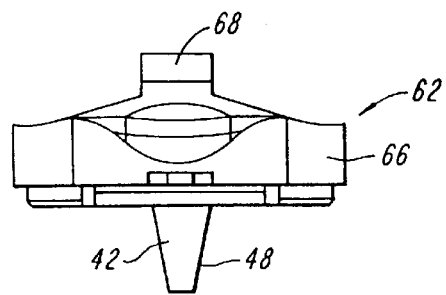
FIG. 6 is an anterior view of another modular tibial bearing insert according to the present invention.
Figure 6A:
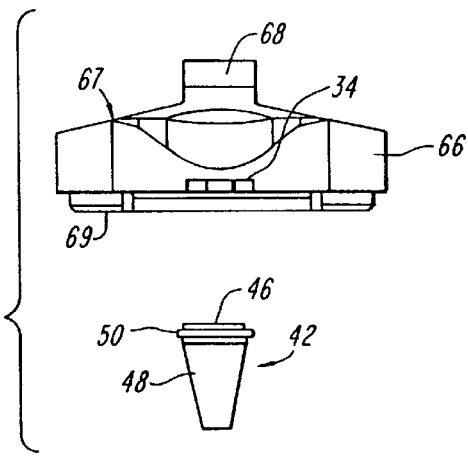
FIG. 6A is an exploded view of the tibial bearing insert of FIG. 6 showing a tibial insert body and a modular rotatable platform element.

FIGS. 5–6A illustrate tibial insert bodies and modular elements that can be used to form rotatable and non-rotatable cruciate substituting tibial bearing inserts 62, 64. The same tibial insert bodies 66 are used to form both the rotatable and non-rotatable cruciate substituting tibial bearing inserts 62, 64. The tibial insert body 66 includes a top surface 67 having a raised spine member 68 of a type known to those having ordinary skill in the art, and a bottom surface 69 having a cavity 34 formed therein. The spine member 68 may protrude above the top surface 67 by a distance of about 5 to 30 mm.

Figure 5A:
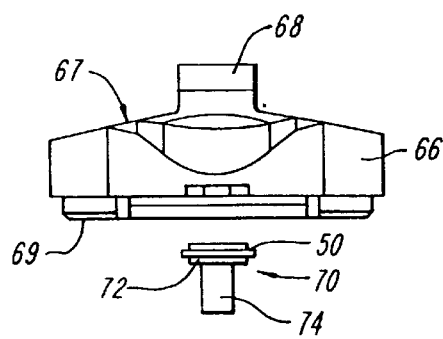
FIG. 5A is an exploded view of the modular tibial bearing insert of FIG. 5 showing the tibial insert body and a modular pin element.

The modular element can be selected to control whether the resulting tibial bearing insert is rotatable or non-rotatable. As shown in FIGS. 5 and 5A, the modular element used to obtain a non-rotatable cruciate substituting tibial insert is a modular pin element 70. Modular pin element 70 has a first plug portion 72 and a distal pin portion 74 extending therefrom. The plug portion 72 may be similar in structure and dimensions to that described above with respect to the plug portion 46 of the modular rotatable platform post 42. Regardless of the geometry selected for the plug portion 46, its dimensions must be sufficient to allow for a secure fit within the cavity 34 to provide secure attachment of the modular pin element 70 to the tibial insert body 66.

The pin portion 74 of the modular pin element 70 that extends distally from the plug portion 72 preferably is of a cylindrical shape having a length of about 10 to 35 mm and a substantially constant diameter in the range of about 4 to 12 mm.

The tibial insert body 66 and the modular pin element 70 may be assembled together to yield the non-rotatable tibial bearing insert 64 of the type shown in FIG. 5. This tibial bearing insert 64 may be mounted upon a suitable tibial plateau in a manner well known in the art to yield a non-rotatable tibial component of a knee prosthesis.

Figure 5B:
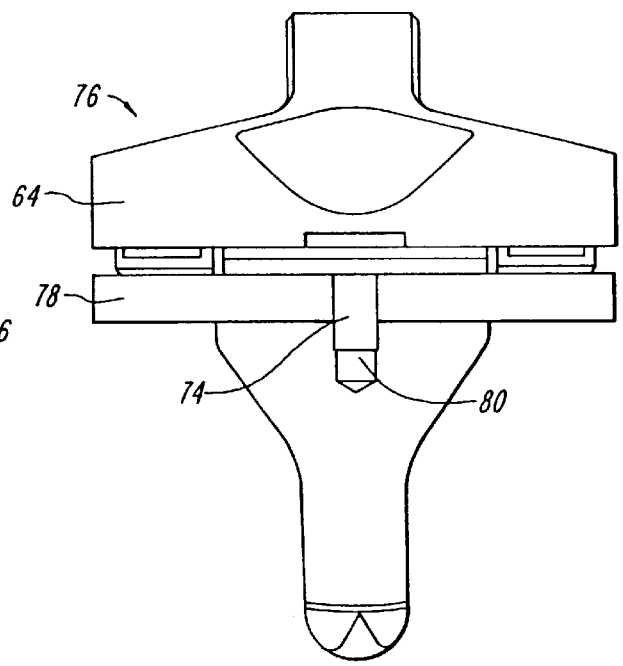
FIG. 5B is an anterior view of the modular tibial bearing insert of FIG. 5 mounted upon a tibial plateau.

FIG. 5B illustrates a tibial component 76 of a knee prosthesis in which a non-rotatable cruciate substituting tibial bearing insert 64 is mounted upon a tibial plateau 78. Tibial plateau 78 is similar to that described above and shown in FIG. 4, except that top surface 54 includes a bore 80 that is non-tapered. The dimensions of cavity 80 should be such that upon seating the pin portion of modular pin element 70 within cavity 80, a slip fit is achieved. The application of further force causes the snap-fit mating of surface features on the tibial bearing insert and the tibial plateau, in a manner known in the art, so that these components are joined together to prevent rotation of the tibial bearing insert independent of the tibial plateau.

FIGS. 6 and 6A illustrate a rotatable cruciate substituting tibial bearing insert 62 formed from a tibial insert body 66 and a modular rotatable platform post 42. The tibial insert body 66 is as described above with respect to the same component illustrated in FIGS. 5 and 5A. This tibial bearing insert body 66 can be modified by the addition of modular rotatable platform post 42 to form a rotatable cruciate substituting tibial bearing insert 62.

The modular rotatable platform post 42 is the same as that described above with respect to FIGS. 3 and 3A. Further, the rotatable cruciate substituting tibial bearing insert 62 may be mounted upon a tibial plateau of type shown in FIG. 4 to achieve a rotatable tibial component of a knee joint prosthesis.

FIGS. 7–9A illustrate modular components of the present invention configured to form rotatable and non-rotatable stabilizing tibial bearing inserts 82, 84 of a knee joint prosthesis system.

Figure 7:
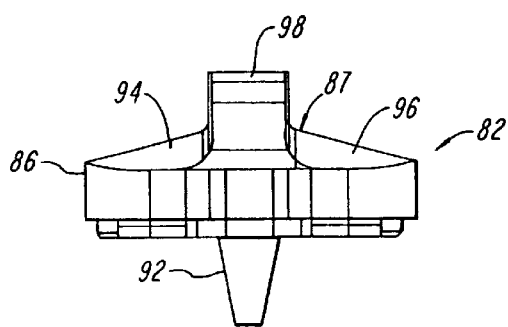
FIG. 7 is a posterior view of another modular tibial bearing insert according to the present invention.
Figure 7A:
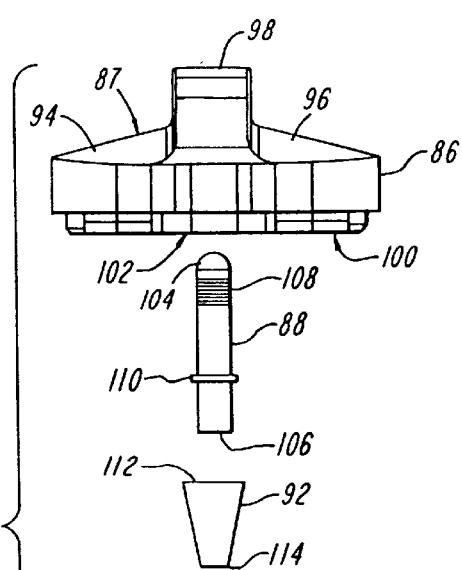
FIG. 7A is an exploded view of the modular tibial bearing of FIG. 7, showing a modular stabilizing pin and a rotatable platform post insert element.
Figure 8:
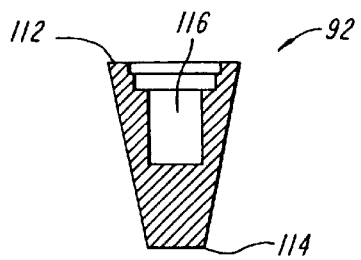
FIG. 8 is a sectional view of the rotatable platform post insert element shown in FIG. 7A.

A fully assembled rotatable stabilizing tibial bearing insert 82 is shown in FIG. 7. Rotatable stabilizing tibial bearing insert 82, as shown in FIGS. 7 and 7A, includes a stabilizing tibial insert body 86 and a stabilizing pin 88. A modular rotating platform post insert element 92 may be used to render the insert rotatable with respect to a tibial plateau element.

The stabilizing tibial insert body 86 includes a top, articulating surface 87 having cavities 94, 96 and a spine element 98 that protrudes therefrom. The bottom surface 100 of insert body 86 includes a cavity 102 (FIG. 9A) which may extend partially into the spine element 98.

Figure 9:
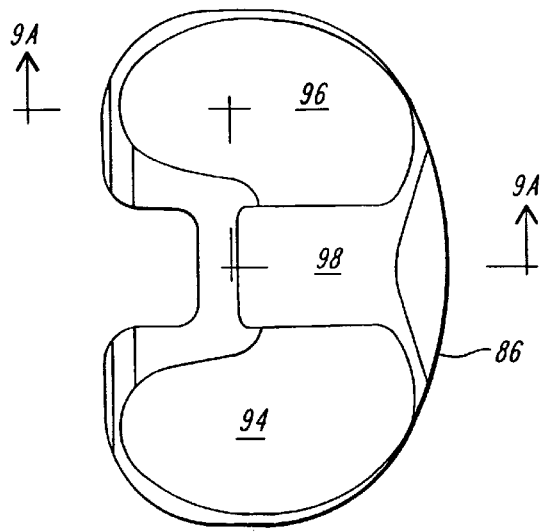
FIG. 9 is a top view of a joint prosthesis system according to the present invention having a non-rotatable modular stabilizing tibial bearing insert mounted upon a tibial plateau.
Figure 9A:
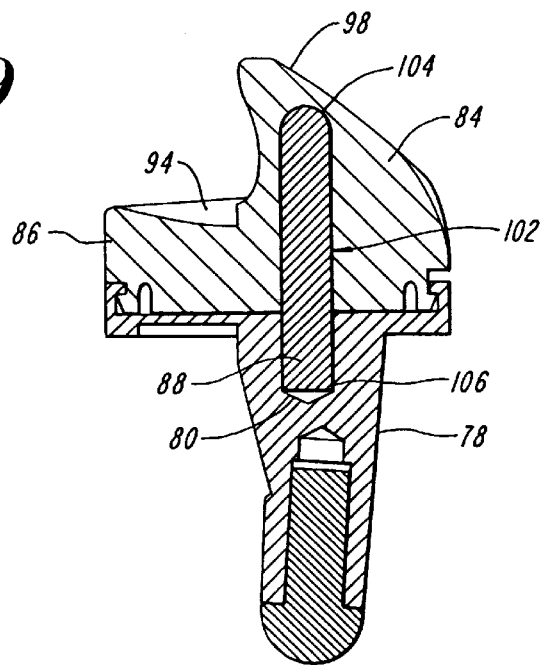
FIG. 9A is a section view of the joint prosthesis of FIG. 9 at line 9A—9A.

The stabilizing pin 88 includes a proximal end 104, which may be rounded, and a distal end 106. Preferably the pin 88 has a length greater than the depth of cavity 102 to enable a distal part of pin 88 to protrude from the insert body 88, as shown in FIG. 9A. The length of the pin 88 is preferably in the range of about 15 to 70 mm and the depth of the cavity 102 is in the range of about 5 to 35 mm. Thus, the pin 88 should protrude from the insert body by a distance of about 10 to 35 mm.

To assemble the tibial bearing insert, pin 88 is inserted the cavity 102 to form an interference fit. The pin 88 may include one or more circumferential ribs 108 (or other surface features, not shown) to enhance securement of the pin and cavity 102. In addition, the pin 88 may include a distal rib 110 to ensure that the pin is fully inserted into the tibial insert body 86.

The cavity preferably has a diameter in the range of about 3 to 7 mm. The pin preferably has a diameter in the range of about 3 to 7 mm in the non-ribbed region and the diameter of about 3.5 to 8 mm when measured from rib to rib.

Modular rotatable platform post insert 92 may be used to form a rotatable stabilizing tibial bearing insert 82. Post insert 92, as shown in FIGS. 7A and 7B, is a frustoconical member having a proximal and distal ends 112, 114 and a length in the range of about 10 to 60 mm. The diameter of the post insert tapers distally from a widest portion in the range of about 10 to 25 mm to a narrowest portion in the range of about 5 to 20 mm. Rotatable post may be substantially solid, except for a cavity 116 that is formed in the proximal end. The cavity 116 should have dimensions sufficient to receive the protruding portion of the stabilizing pin 88 in a secure interference fit. The cavity 116 preferably has a depth of about 5 to 40 mm and a diameter of 3 to 7 mm. The modular rotatable platform post 92 may be secured to the pin 88 by snap-fitting the proximal end 112 over rib 110 of pin 88.

Upon assembly of the modular components to form rotatable stabilizing tibial bearing insert 82, the insert 82 may be joined to a tibial plateau 52 of the type shown in FIG. 4. Tibial plateau 52, as noted above, includes a tapered bore 60 which seats rotatable post element 92 to enable rotation of the tibial bearing insert element 82 relative to the tibial plateau 52.

A non-rotatable stabilizing tibial bearing insert 84 may also be formed from the components described above by omitting the modular rotatable platform post insert element 92. FIGS. 9 and 9A illustrate a non-rotatable stabilizing tibial bearing insert 84 to tibial plateau 78. As shown, the stabilizing pin 88 is joined within bore 102 such that the proximal end 104 thereof is disposed within the spine 98 and the distal end 106 protrudes from the insert body 86. The non-rotatable stabilizing tibial bearing insert 84 component is joined to a tibial plateau 78 of the type shown in FIG. 5B such that the protruding distal portion of the stabilizing pin 88 forms a slip fit within bore 80 of the tibial plateau. The application of further force causes the tibial bearing insert and the tibial plateau to be joined together in a snap fit, in a manner known in the art, to prevent rotation of the tibial bearing insert 84 relative to the tibial plateau 78. To facilitate this slip fit between pin 88 and cavity 80, the cavity 80 should be non-tapered, having a substantially constant diameter in the range of about 3 to 7 mm.

It is understood that various modifications may be made to the invention described herein and without departing from its intended scope.

What is claimed is:

1. A modular joint prosthesis system, comprising:
    a tibial insert body having a top, articulating surface and a bottom, mating surface;
    a tibial plateau having a bottom, bone engaging surface and a top surface matable with the bottom surface of the tibial insert body;
    a cavity formed in the mating surface of the tibial insert body; and
    a plurality of modular elements, at least one of which forms a rotatable prothesis system and at least another of which forms a non-rotable prosthesis system, the modular elements being matable within the cavity of the tibial insert body to yield insert having a different functionality.

2. The system of claim 1, wherein a non-tapered cavity is formed in the top surface of the tibial plateau.

3. The system of claim 2, wherein the tibial insert body is suitable for use as a non-rotatable cruciate substituting tibial insert, and the top surface thereof includes a protruding spine element and at least one condylar recess, and wherein one of the plurality of modular insert elements is a modular pin element having a proximal plug portion and a distal pin portion matable within the cavity of the tibial insert body such that the distal pin portion protrudes from the bottom surface of the tibial insert body and is adapted to mate within the non-tapered cavity formed within the top surface of the tibial plateau.

4. The system of claim 3, wherein the distal pin portion has a length in the range of about 10 to 35 mm and a diameter in the range of about 4 to 12 mm.

5. The system of claim 3, wherein the spine element protrudes from the top surface of the tibial insert body by about 5 to 30 mm.

6. The system of claim 2, wherein the tibial insert body is suitable for use as a non-rotatable stabilized tibial insert, and the top surface thereof includes a protruding spine element and at least one condylar recess, and wherein the cavity formed in the mating surface of the tibial insert body extends at least partially into the spine element.

7. The system of claim 6, wherein one of the plurality of modular insert elements is an elongate stabilizing pin having a proximal end matable in an interference fit within the cavity formed in the mating surface of the tibial insert body and a distal end that protrudes from the tibial insert body when the stabilizing pin is mated within the cavity formed in the mating surface of the tibial insert body, the distal end of the stabilizing pin being adapted to mate in a slip fit within the non-tapered cavity formed within the top surface of the tibial plateau.

8. The system of claim 7, wherein a proximal portion of the stabilizing pin includes a plurality of circumferential ribs.

9. The system of claim 7, wherein the stabilizing pin has a length in the range of about 15 to 70 mm and a diameter in the range of about 3 to 7 mm.

10. The system of claim 8, wherein the distal end of the stabilizing pin protrudes from the tibial insert body by a distance of about 5 to 35 mm, when the stabilizing pin is mated within the cavity of the tibial insert body.

11. The system of claim 1, wherein a distally tapered cavity is formed in the top surface of the tibial plateau.

12. The system of claim 4 wherein the tibial insert body is suitable for use as a rotatable cruciate retaining tibial insert and the top surface thereof includes at least one condylar recess, and wherein one of the plurality of modular insert elements is a modular rotating platform post having a first, plug portion matable with the cavity of the tibial insert body and a second, frustoconical portion extending distally from the plug portion, the frustoconical portion tapering distally from the plug portion and being matable within the distally tapered cavity formed in the top surface of the tibial plateau to permit rotation of the tibial insert body with respect to the tibial plateau.

13. The system of claim 12, wherein the length of the frustoconical portion of the modular rotating platform post is in the range of about 10 to 50 mm, and the diameter of the frustoconical portion of the modular rotating platform post is in the range of about 10 to 25 mm at its widest point, and in the range of about 5 to 20 mm at its narrowest point.

14. The system of claim 11, wherein the tibial insert body is suitable for use as a rotatable cruciate substituting tibial insert and the top surface thereof includes a protruding spine element and at least one condylar recess, and wherein one of the plurality of modular insert elements is a modular rotating platform post having a first, plug portion matable within the cavity of the tibial insert body and a second, frustoconical portion extending distally from the portion and being matable within the distally tapered cavity formed in the top surface of the tibial plateau to permit rotation of the tibial insert body with respect to the tibial plateau.

15. The system of claim 14, wherein the length of the frustoconical portion of the modular rotating platform post is in the range of about 10 to 50 mm and the diameter of the frustoconical portion of the modular rotating platform post is in the range of about 10 to 25 mm at its widest point, and in the range of about 5 to 20 mm at its narrowest point.

16. The system of claim 14, wherein the tibial insert body is suitable for use as a rotatable stabilized tibial insert and the top surface thereof includes a protruding spine element and at least one condylar recess, and wherein the cavity formed in the mating surface of the tibial insert body extends at least partially into the spine element.

17. The system of claim 16, wherein one of the plurality of modular insert elements is an elongate stabilizing pin having a proximal end matable in an interference fit within the cavity formed in the mating surface, the tibial insert body and a distal end of the elongate stabilizing pin protrudes from the tibial insert body when the stabilizing pin is mated within the cavity formed in the mating surface of the tibial insert body.

18. The system of claim 17, wherein the distal end of the stabilizing pin protrudes from the tibial insert body by a distance of about 5 to 35 mm, when the stabilizing pin is mated within the cavity of the tibial insert body.

19. The system of claim 18, further comprising a modular rotating platform post insert element having a frustoconical, distally tapered outer surface and proximal and distal ends, the proximal end thereof having a cavity formed therein for mating in an interference fit with the distal end of the stabilizing pin, and the distal end thereof being rotatably matable within the distally tapered cavity formed in the top surface of the tibial plateau to permit rotation of the tibial insert body with respect to the tibial plateau.

20. The system of claim 19, wherein the length of the modular rotating platform post insert element is in the range of 10 to 60 mm.

21. The system of claim 20, wherein the modular rotating platform post insert element has a diameter at its widest point in the range of about 10 to 25 mm and a diameter at its narrowest point in the range of about 5 to 20 mm.

22. The system of claim 21, wherein the stabilizing pin has a length in the range of about 15 to 70 mm.

23. The prosthesis of claim 1, wherein the tibial insert body is suitable for use as a non-rotatable cruciate retaining tibial insert and the top surface thereof includes at least one condylar recess, and wherein one of the plurality of modular insert elements is a spacer plug having a top surface matable within the cavity and a bottom surface that is substantially flush with the mating surface of the tibial insert body when mated within the cavity.

* * * * *